US005972638A

United States Patent [19]
Burlage et al.

[11] Patent Number: 5,972,638
[45] Date of Patent: *Oct. 26, 1999

[54] METHOD FOR DETECTION OF BURIED EXPLOSIVES USING A BIOSENSOR

[75] Inventors: Robert S. Burlage, Knoxville; David R. Patek, Loudon; Kirk R. Everman, Knoxville, all of Tenn.

[73] Assignee: Lockheed Martin Energy Research Corp., Tenn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/792,251

[22] Filed: Jan. 31, 1997

[51] Int. Cl.$^6$ .............................. C12N 1/21; C12Q 1/02; C12Q 1/24

[52] U.S. Cl. ............................ 435/29; 434/4; 434/252.3; 434/252.31; 434/252.33

[58] Field of Search ...................... 435/4, 252.3, 252.31, 435/252.33, 254.11, 29

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 4,965,188 | 10/1990 | Mullis et al. | 435/6 |
| 5,491,084 | 2/1996 | Chalfie et al. | 435/189 |

OTHER PUBLICATIONS

Hogan et al., "Environmental Influences on Mine Detection," Special Report 90–31, Aug. 1990, Cold Regions Research & Engineering Laboratory.
Pennington et al., "Effects of Wet and Dry Cycles on TNT Losses from Soils," Technical Report EL–92–37, U.S. Army Engineer Waterways Experiment Station, Vicksburg, MS.
Phelan and Webb, "Environmental Fate and Transport of Chemical Signatures from Buried Landmines—Screening Model Formulation and Initial Simulations," Sandia National Report SAND97–1426, UC–741, Jun. 1997.
Heim et al., "Wavelength mutations and posttranslational autoxidation of green fluorescent protein," *Proc. Natl. Acad. Sci. USA* 91: 12501–12504 (1994).
Walsh and Jenkins, "Identification of TNT Transformation Products in Soil," *U.S. Army Corps of Engineers Special Report* 92–16, Jun., 1992.
Duque et al., "Construction of a Pseudomonas Hybrid Strain that Mineralizes 2,4,6–trinitrotoluene," *J. Bacteriol.* 175:2278–2283 (1993).
Boopathy and Kulpa, "Nitroaromatic compounds serve as nitrogen source for Desulfovibrio sp. (B strain)," *Can. J. Microbiol.* 39: 430–433 (1993).
Haïdour and Ramos, "Identification of Products Resulting from the Biological Reduction of 2,4,6–trinitrotoluene, 2,4–Dinitrotoluene, and 2,6–Dinitrotoluene by Pseudomonas Sp.," *Environ. Sci. Technol.*, 30:2365–2370 (1996).

Higson, "Microbial Degradation of Nitroaromatic Compounds," *Adv. App. Microbiol.*, 37:1–19 (1992).
Vorbeck et al., "Intitial Reductive Reactions in Aerobic Mineral Metabolism of 2,4,6–trinitrotoluene," *Appl. Environ. Microbiol.*, 64:246–252 (1996).
Alvarez et al., "*Pseudomonas aeruginosa* Strain MA01 Aerobically Metabolizes the Aminodinitrotoluenes Produced by 2,4,6–trinitrotoluene Nitro Group Reduction," *Can. J. Microbiol.*, 41:984–991 (1995).
Spain, "Biodegradation of Nitroaromatic Compounds," *Ann. Rev. Microbiol.*, 49:523–555 (1995).
Martin et al., "Denitration of 2,4,6–trinitrotoluene by *Pseudomonas savastanoi*," *Can. J. Microbiol.*, 43:447–455 (1997).
Schackmann and Müller, "Reduction of Nitroaromatic Compounds by Different Pseudomonas Species Under Aerobic Conditions," *Appl. Microbiol. Biotechnol.*, 34:809–813 (1991).
Jenkins et al., "Liquid Chromatographic Method for Determination of Extractable Nitroaromatic and Nitramine Residues in Soil," *J. Assoc. Off. Anal. Chem.* 72:890–899 (1989).
Fiorella and Spain, "Transformation of 2,4,6–trinitrotoluene by *Pseudomonas pseudoalcaligenes* JS52," *Appl. Environ. Microbiol.*, 63:2007–2015 (1997).
Pasti–Grigsby et al., "Transformation of 2,4,6–trinitrotoluene (TNT) by Actinomycetes Isolated from TNT–Contaminated and Uncontaminated Environmental," *Appl. Environ. Microbiol.*, 62:1120–1123 (1996).
Lewis et al., "Products of Anaerobic 2,4,6–trinitrotoluene (TNT) Transformation by *Clostridium bifermentans*," *Appl. Environ. Microbiol.*, 62:4669–4674 (1996).
Bruns–Nagel et al., "Microbial Transformation of 2,4, 6–trinitrotoluene in Aerobic Soil Columns," *Appl. Environ. Microbiol.*, 62:2651–2656 (1996).
Williams et al., "Composting of explosives and propellant contaminated soils under thermophilic and mesophilic conditions," *J. Ind. Microbiol.* 9: 137–144 (1992).
Dawel et al., "Structure of a Laccase–Mediated Product of Coupling of 2,4–Diamino–6–Nitrotoluene to Guaiacol, a Model for Coupling of 2,4,6–Trinitrotoluene Metabolites to a Humic Organic Soil Matrix," *Appl. Environ. Microbiol.* 63: 2560–2565 (1997).
Spencer et al., "Soil–Pesticide Interactions and Their Impact on the Volatilization Process," in *Environmental Impacts of Soil Component Interactions*—Land Quality, Natural and Antropogenic Organics, Huang (ed.), pp. 371–382, CRC Press, Inc. (1995).

(List continued on next page.)

Primary Examiner—Johnny F. Railey, II
Attorney, Agent, or Firm—Medlen & Carroll, LLP

[57] ABSTRACT

The present invention provides a method for detecting buried explosives which exude vapors of the explosive chemical to the surface. A biological sensor that is applied on the surface produces a detectable signal when it is contacted by the explosive chemical, producing an identifiable pattern for pin-pointing the explosive. The biological sensor is a genetically altered organism.

39 Claims, 5 Drawing Sheets

OTHER PUBLICATIONS

Andreux et al., "Factors Affecting the Movements, Reactions, and Biotransformations of Xenobiotics," in *Environmental Impacts of Soil Component Interactions*—Land Quality, Natural and Antropogenic Organics, Huang (ed.), pp. 371–382, CRC Press, Inc. (1995).

Defense Threat Reduction Agency, Test Report for the Microbial Mine Detection System (MMDS), DSWA IACRO HD1102–8–1490–097, 15 Nov. 1998.

R. S. Burlage et al., "Development and Application of the lux Gene for Environmental Bioremediation," *Society Of Photo–Optical Instrumentation Engineers,* 2835: 42–51 (1996).

Prasher et al., "Primary Structure of the *Aequorea Victoria* Green–Fluorescent Protein," *Gene* 111: 229–233 (1992).

Chalfie et al., "Green Fluorescent Protein as a Marker for Gene Expression," *Science* 263: 802–805 (1994).

Lorenz et al., "Isolation and Expression of a cDNA Encoding *Renilla Reniformis* Luciferase," *Proc. Natl. Acad. Sci.* 88: 4438–4442 (1991).

SanPietro et al., "Sequence of the Chromogenic Hexapeptide of Renilla Green–Fluorescent Protein," Abstracts 21st Annual Meeting of the American Society for Photobiology (Jun. 1993).

Edward A. Meighen, "Molecular Biology of Bacterial Bioluminescence," *Microbiological Reviews,* 55: 123–126 (1991).

E.A. Meighen, "Genetics of Bacterial Bioluminescence," *Annu. Rev. Genet* 28: 117–139 (1994).

Sambrook et al., *Molecular Cloning, a Laboratory Manual,* Cold Spring Harbor Laboratory Press (1989).

de Lorenzo et al., "Mini–Tn5 Transposon Derivatives for Insertion Mutagenesis, Promoter Probing, and Chromosomal Insertion of Cloned DNA in Gram–Negative Eubacteria," *Journal of Bacteriology,* 172: 6568–6572 (1990).

Simon et al., "New Derivatives of Transposon Tn5 Suitable for Mobilization of Replicons, Generation of Operon Fusions and Induction of Genes in Gram–Negative Bacteria," *Gene* 80: 161–169 (1989).

Akbar et al., "Isolation and Characterization of csbB, a Gene Controlled by *Bacullus Subtilis* General Stress Transcription Factor $\delta^B$," *Gene* 177: 123–128 (1996).

M. Fuller et al., "Microbial Ecology of Soil Slurries Degrading 2,4,6–Trinitrotoluene (TNT)," Abstracts, 96th Annual Meeting of the American Society for Microbiology (May, 1996).

Parales et al., "Genetic Engineering Changes the Substrate Oxidation Profile of 2–Nitrotoluene 2,3–Dioxygenase," Abstracts, 96th Annual Meeting of the American Society for Microbiology (May, 1996).

Fiorella et al., "Transformation of TNT by Pseudomonas Pseudoalcaligenes Strain JS45," Abstracts, 96th Annual Meeting of the American Society for Microbiology (May, 1996).

Noguera et al., "Cometabolic Biotransformation of Nitroaromatic Compounds by a *Psuedomonas Geruginosa* Strain," Abstracts, 96th Annual Meeting of the American Society for Microbiology (May, 1996).

Funk et al., "Biodegradation of TNT by a Strain of Clostridium Bifermentens," Abstracts, 96th Annual Meeting of the American Society for Microbiology (May, 1996).

Alatriste–Mondracon et al., "Degradation of Hexahydro–1,3,5–trinitro–1,3,5–Triazine (RDX) by *Clostridium Putrificum,*" Abstracts, 96th Annual Meeting of the American Society for Microbiology (May, 1996).

Winship et al., "Fungal Bioremediation of Explosives Contaminated Soil," Abstracts, 96th Annual Meeting of the American Society for Microbiology (May, 1996).

Blehert et al., "Bacterial Degradation of Nitroglycerin," Abstracts, 96th Annual Meeting of the American Society for Microbiology (May, 1996).

Binks et al., "Degradation of Hexahydro–1,3,5–Trinitro–1,3,5–Triazine (RDX) by *Stenotrophomonas Maltophilia* PBI," *Applied and Environmental Microbiolgy,* 61: 1318–1322 (1995).

Robert.S. Burlage et al., "A Transposon For Green Fluorescent Protein Trancriptional Fusions: Application For Bacterial Transport Experiments," *Gene,* 173: 53–58 (1996).

Robert S. Burlage et al., "Monitoring of Naphthalene Catabolism by Bioluminescence With Nah–lux Transcriptional Fusions," *Journal of Bacteriology,* 172: 4749–4757 (1990).

J.M.H. King et al., "Rapid, Sensitive Bioluminescent Reporter Technology for Naphthalene Exposure and Biodegradation," *Science,* 249: 778–781 (1990).

Selifonova et al., "Bioluminescent Sensors For Detection of Bioavailabe Hg(II) in the Environment," *Applied and Environmental Microbiology,* 59: 3083–3090 (1993).

Hawari et al., Applied and Environmental Microbiology 64(6):2200–2206 (1998).

Burlage et al., Applied Biochemistry and Biotechnology 45–46:731–740 (1994).

Bronstein et al., Analytical Biochemistry 219:169–181 (1994).

Jain et al., BioTechniques 15(4):600–602 (1993).

Wood et al., Analytical Biochemistry 161:501–507 (1987).

SEQUENCE LISTING

<160> NUMBER OF SEQ ID NOS: 3

<210> SEQ ID NO 1
<211> LENGTH: 10
<212> TYPE: DNA
<213> ORGANISM: synthetic construct

<400> SEQUENCE: 1
agcggccgct                                                          10

<210> SEQ ID NO 2
<211> LENGTH: 23
<212> TYPE: DNA
<213> ORGANISM: Bacillus subtilis

<400> SEQUENCE: 2
ccatccgtct gtcataatgg cag                                           23

<210> SEQ ID NO 3
<211> LENGTH: 22
<212> TYPE: DNA
<213> ORGANISM: Bacillus subtilis

<400> SEQUENCE: 3
tgatctgctg aagcgtgtca tc                                            22

METHOD FOR DETECTION OF BURIED EXPLOSIVES USING A BIOSENSOR

FIELD OF THE INVENTION

This invention relates generally to the detection of explosives. In particular, the invention provides a method and composition for the detection of buried explosives and munitions.

BACKGROUND OF THE INVENTION

The wars of this century have involved the use of massive numbers of high explosive munitions. Shells, bombs, and landmines all function in substantially the same way. A high explosive charge fills the munition housing. This high explosive charge is characterized by its relative stability and insensitivity to shock, handling, and temperature changes. This enables the munitions to be safely handled and transported without the risk of accidental detonation. A small booster or initiator of a more sensitive explosive is typically provided to detonate the high explosive. A fuze is then provided to detonate the booster when a specific event occurs. For example, a bomb fuze may detonate the booster after a specific pre-selected time has elapsed after the bomb has been dropped. Similarly, an artillery fuze may detonate a shell on impact after firing, or at a predetermined height above ground. And the fuze in a landmine will detonate the booster when a predetermined amount of pressure is sensed.

Most munitions function as intended and explode when they are supposed to. However, some munitions malfunction and do not explode. Such munitions are not safe, and often remain buried beneath the surface of the ground, presenting a significant hazard which can render an area so dangerous that it is no longer habitable. Almost eighty years after the end of World War I, there are still areas in France which remain fenced-off due to the danger of unexploded munitions. The greater hazard, of course, occurs in the areas which are still inhabited. Farmers in France still plow up unexploded ordnance; some of them are injured or killed in the process. The same problems exist in other areas of the world where conflicts have raged, from Germany to Africa, and from Kuwait to Bosnia or Vietnam.

Conventional methods of removing buried, unexploded munitions are time consuming and often dangerous. For example, conventional methods often involve the location of the buried, unexploded munitions by an individual who inserts a probe into the soil, until a solid object is encountered. The solid object is excavated, and if found to be an unexploded munition, it can be remotely detonated using a conventional high explosive charge, such as a block of TNT or C-4, placed onto or next to the munition. This method can be risky when the buried munitions contain magnetic fuzes, when the personnel clearing the area are not careful, and when anti-personnel mines are present.

Other conventional methods include remotely detonating explosive charges above the surface of the area thought to contain mines, in an attempt to detonate them, and propelling a heavy weight or roller over the area thought to contain mines (for example, in front of an armored vehicle), to detonate the mines. The primary disadvantages for these methods are (1) it can be dangerous since some mine fuzes can be set to count occurrences, and detonate on the second or subsequent occurrence (i.e., the pressure exerted by the heavy weight is sufficient to count as an occurrence, but doesn't detonate the mine; the pressure exerted by the armored vehicle pushing the weight is also sufficient to count as an occurrence, and will detonate the mine if the fuze is set to detonate on the second occurrence); (2) this method is not very likely to detonate munitions which are buried more deeply than mines (more than 1–2 feet below the surface), or munitions which do not use pressure fuzes.

Accordingly, the need exists for a safe method of detecting buried ordnance so that steps can be taken to remove the hazard by physically removing the ordnance, or by detonating it remotely.

SUMMARY OF THE INVENTION

The invention provides a method and composition for the detection of buried explosives and munitions.

The invention provides a method of detecting explosives buried beneath the surface of the ground, comprising spraying a biological sensor on the surface of the ground in an area believed to contain the buried explosives so that the biological sensor contacts soil; allowing a sufficient time to pass to enable the biological sensor to react with explosive residue in the soil to produce a visually detectable signal; and examining the surface of the area for the visually detectable signal. In one embodiment, the buried explosives comprise unexploded munitions. In a second embodiment, the biological sensor produces a protein which fluoresces after exposure to fluorescence excitation. In a further embodiment, the step of examining the surface is performed by using ultraviolet light to check for fluorescence. In an alternative embodiment, the biological sensor is applied to the surface of the ground during hours of reduced sunlight between twilight and dawn. In another alternative embodiment, the protein produced is a fluorescent protein. With a fluorescent protein, sufficient time to enable the biological sensor to produce the visually detectable signal is from about 2 hours to about 3 days. In still another alternative embodiment, the protein produced is a bioluminescent protein.

In a particular embodiment of the method, the biological sensor is a genetically modified organism selected from the group consisting of bacteria and fungi. More particularly, the biological sensor is a genetically altered bacterium selected from the group consisting of *Pseudomonas putida,* and *Bacillus subtilis.*

The method of the invention additionally includes, as a preliminary step, gently irradiating the area suspected of containing buried explosives with electromagnetic energy in order to increase explosive vapor concentration in the soil above and around the buried explosive, prior to applying the biological sensor to the surface. In this method, the electromagnetic energy varies from high-frequency to long wavelength microwave.

The method of the invention includes an embodiment wherein the step of examining the surface of the area for a visually detectable signal is performed by using a source of ultraviolet light which can be switched on and off in conjunction with a vision system, the vision system comprising a charge coupled device camera operatively connected to a computer for capturing images, and additionally comprising the steps of capturing a first image of an area with the ultraviolet light source turned on, capturing a second image of the area with the ultraviolet light source turned off, and subtracting the first image from the second image to produce a composite image which reveals only objects which fluoresce under the influence of the ultraviolet illumination.

The invention also provides for a biological sensor for detecting explosives comprising a recombinant bacterial strain that responds to contacting a chemical from an explosive by producing a detectable signal. In another embodiment of the biological sensor, a bacterial cell of the recombinant bacterial strain comprises a regulatory element from a gene that is inducible by the chemical, the regulatory element being operably linked to a bioreporter sequence encoding a protein that functions to produce the detectable signal. In a further embodiment, the protein produces a fluorescent signal. In an alternative embodiment the protein produces a bioluminescent signal.

DESCRIPTION OF THE INVENTION

Figure 1:
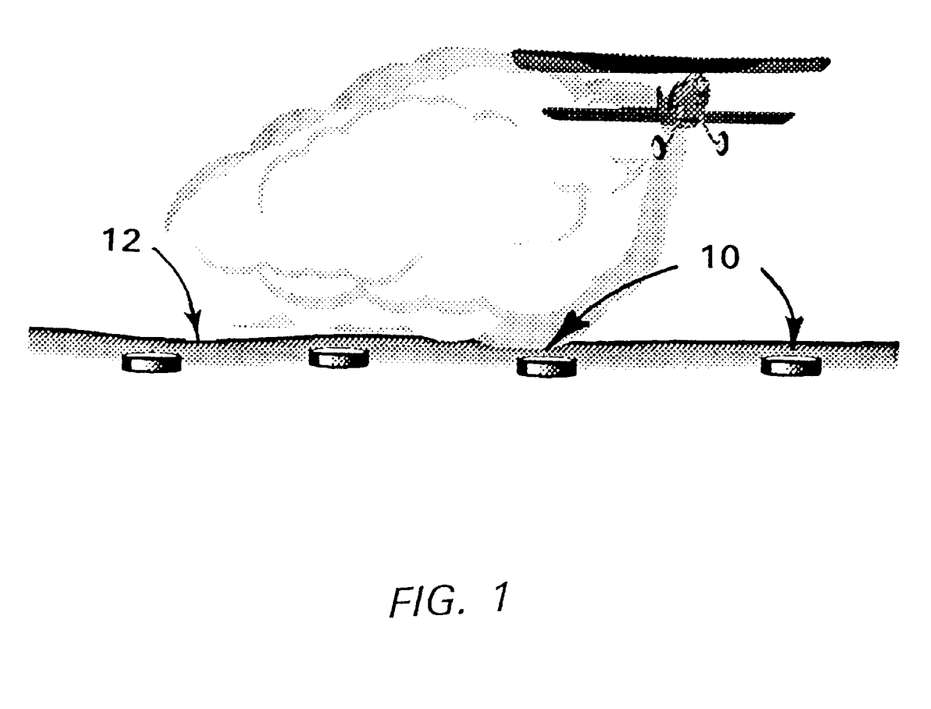
FIG. 1 is a cross-section showing an unexploded munition buried beneath the surface of the ground.

In a method of the present invention, as shown in FIG. 1, a biological agent or sensor is used to detect conventional explosives, which may be contained in unexploded munitions 10 buried below the surface of the ground 12. Such munitions exude or leak vapors of the explosive. These vapors are typically concentrated in surrounding soil and migrate to the surface. This leakage often occurs with conventional munitions which contain, for example, trinitrotoluene ("TNT"), hexahydro-1,3,5-trinitro-1,3,5-triazine ("RDX"), and octahydro-1,3,5-trinitro-1,3,5,7-tetrazocine ("HMX"). A biological sensor of the present invention is one which reacts with the explosive residue or vapor to produce a visual signal on the surface of the ground 12 above the buried munition 10. Preferably, the biological sensor is one in which exposure to the explosive vapors results in the production of a protein which fluoresces when exposed to excitation light, such as ultraviolet (UV) light.

In another method of the invention two biological agents are used in concert to produce an amplified detectable signal. For example, two microorganisms may be used. The first strain of microorganism senses the chemical from the explosive and, in response, produces a large quantity of a substance (an effector molecule) that is transported or diffuses freely into the surrounding environment, where the second strain of microorganism is located. The second strain of microorganism (the bioreporter) detects the substance and responds by producing a detectable signal. The advantage of this method is that the first strain of microorganism produces a multitude of secondary effector molecules, which can induce a multitude of organisms of the second strain. Thus, there is a cascade effect. The bioreporter strain is most likely constructed by bioengineering. The first strain of microorganism may be one that is naturally occurring or may be bioengineered, as well.

The method using two microorganisms can be further illustrated. A first microorganism responds to TNT by producing enzymes that catabolize TNT. The first microorganism is bioengineered so that the genes encoding the catabolic enzymes are fused to a gene encoding an iron-scavenging protein. Thus, in response to molecules of TNT, the genes encoding the catabolic enzymes are induced and this also induces the gene for the iron-scavenging protein. This protein is transported outside the cell where the soil contains iron, which binds to the iron-scavenging protein. The second strain of microorganism is bioengineered to have no scavenger protein (it is always starved for iron) and has a receptor for the scavenger protein that is always induced for scavenger protein uptake. Therefore, the second strain brings the loaded iron-scavenging protein into the cell and the presence of the iron induces an iron-sensitive gene, which is fused to a bioreporter gene.

In another embodiment of the method of the invention, the biosensor produces a protein which requires reaction with a substrate to produce the detectable signal. In this embodiment of the method, both the biosensor and the substrate are spread over the terrain. The biosensor utilizes the substrate in a reaction with the protein to produce the signal.

Growing the Biological Sensor

A recombinant biological sensor is constructed as described below. Once the biological sensor has been constructed, it can be stored, if desired, using conventional methods such as, for example, freezing or lyophilizing (freeze drying). A starter culture can be grown in 100 ml of medium in a sterile flask. If frozen or freeze-dried, the culture is first revived on agar minimal medium without antibiotic. This is used to inoculate the medium in the large-scale growth vessel (about $10^8$ to about $10^{10}$ bacteria is generally an adequate inoculum).

If the biological sensor is a bacterial strain, it can be grown in large volumes using a bioreactor—a container and a stirring device. A 55 gallon drum, which is commonly available almost everywhere in the world, can be used as the container. The container is filled to about 45 gallons with a buffered solution (generally, a pH of about 7.0 to about 7.5 is adequate), simple mineral salts, a carbon, nitrogen and phosphate source, and trace minerals, (e.g., Davis minimal broth: $K_2HPO_4$, $KH_2PO_4$, $(NH_4)_2SO_4$, glucose, sodium citrate, $MgSO_4.7H_2O$). A buffering agent may be used to bolster the buffering capacity of the medium, if necessary. One skilled in the art will be able to determine if there is a need to add specific growth additives, depending upon the strain of bacteria selected. A commercial variable speed mixer is preferably used to gently stir the tank. Typically, cultures are shaken at 100–150 rpm, however, stirring may also be accomplished by hand in the field, if necessary. Oxygen can be bubbled in through a hose that pumps in filtered air. Power requirements are very low. All of the requirements can be met by a typical army field kitchen.

The most preferred bacterial strains grow well at ambient temperatures found in temperate climates. A typical temperature range for the growth of the bacteria is about 15° C. to about 30° C. Sufficient bacterial growth occurs within 24 hours, at which time the concentration of the cells is checked using any conventional device such as, for example, a Klett meter which measures light scattering which is proportional to the number of cells present. A concentration of about $10^8$ bacteria per ml (or about $3.7 \times 10^{11}$ bacteria/gallon U.S.) is sufficient for the purposes of this invention. The bacterial solution is preferably loaded into a dispensing system and sprayed over the area to be checked for unexploded munitions within the next 1–2 hours. Waiting longer could cause clogging of the spray heads, since the bacteria tend to settle out.

Using the Biological Sensor to Detect Buried Explosives

Figure 2:
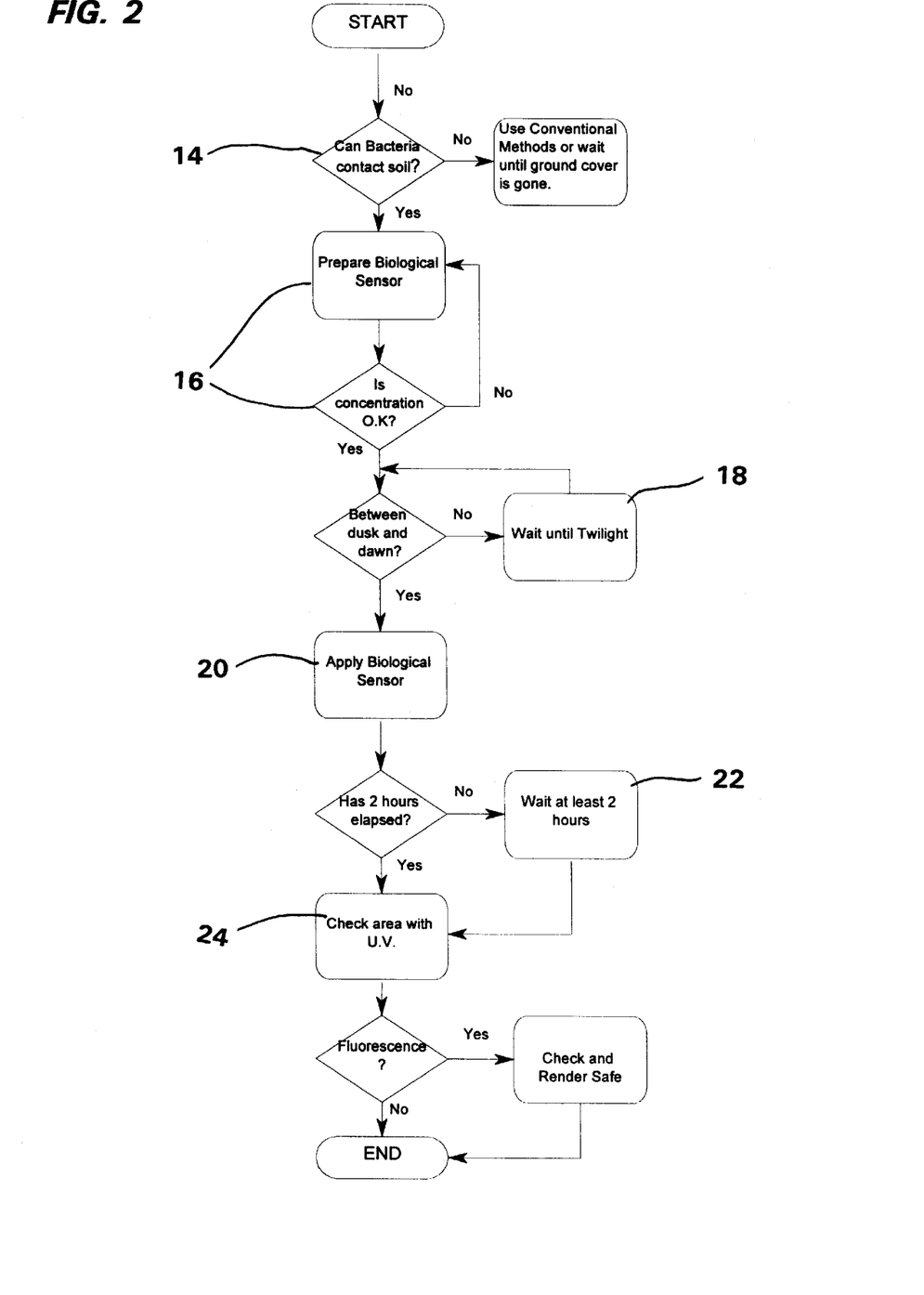
FIG. 2 is a diagram showing a method of the present invention.

As shown in FIG. 2, the present method begins with an analysis of the area suspected to contain buried explosives or munitions. As a preliminary matter, shown as step 14, the area is surveyed to determine if there is ground cover, such as snow, ice, or water, which would prevent the biological sensor from coming in contact with the soil. If this is the case, conventional methods of detecting buried munitions must be used or the method is reinitiated when the ground is suitable. Assuming there is no inhibiting ground cover, the next step 16 is to prepare (i.e., grow) the biological sensor.

A biological sensor of the present invention reacts with explosive residue and vapors to produce a visual signal. In the preferred embodiment, the biological sensor is a genetically recombinant bacterial strain which reacts with molecules of the explosive in the soil to produce Green Fluorescent Protein (GFP) which fluoresces under UV light. The particular recombinant organism selected as the biological sensor will produce the desired signal when exposed to particular explosives with which the organism will react. However, a single strain, such as a single bacterial strain, while it may produce a very strong signal with some explosives, may not react well (or at all) with all explosives which may be buried in a given area. Therefore, in the event of the development of new explosives, or the use of explosives not commonly encountered, or the desire to use a sensor which reacts strongly to a variety of explosives, it may be desirable to formulate a "cocktail" or mixture of two or more different biological sensors so that all of the explosives which may be buried in a particular area can be detected.

To obtain a good, detectable signal, the concentration of recombinant organisms must be sufficient. Accordingly, as provided in step 16, the concentration is checked. If the concentration is not sufficient, growth of the cells should be continued, or, the user should start over with a new preparation. The appropriate concentration and the optimal strain for a recombinant biosensor organism will vary with different environmental parameters (e.g., desert, cultivated area, shoreline). One skilled in the art will be able to determine the necessary adjustments.

The preferred biological sensor is most preferably applied at twilight, as indicated at step 18 of FIG. 2. This is because the bacteria comprising the preferred sensor will likely be killed by sunlight, and because it is more difficult to detect the UV-induced fluorescence caused by the GFP during daylight. Accordingly, the method of the present invention using the preferred biosensor should be carried out between twilight and dawn.

As indicated by step 20, the bacterial solution containing the preferred sensor is then applied to the ground surface of a suspected area. Application can be by conventional spray techniques. These include aircraft mounted sprayers, truck mounted sprayers, or spraying equipment carried and operated by an individual, including hand-held sprayers. The goal is to apply approximately 1000 bacteria per square centimeter of the surface to be checked. Thus, the bacteria grown as described above in a 55 gallon drum should be sufficient to check approximately 100 acres. As noted above, the bacteria must contact the ground surface in order to react with any explosive residue or vapors contained in the soil.

Once the bacterial solution has been applied to the soil surface, the bacteria should be allowed to react with any explosive residue or vapor which is found in the soil. Time is allowed for the production of a detectable signal. With the preferred sensor, as indicated at step 22, this takes at least about 2 hours. With a bioluminescent signal, the time is about 1 hour. However, if desired, the area can be checked for the identifiable signal up to three days after the bacteria are applied. After the waiting period has elapsed, the surface of the area can be checked using conventional ultraviolet radiation, as shown at step 24 of FIG. 2. For example, GFP fluoresces at a wavelength of about 509 nm when excited by UV. Thus, individuals using hand-held UV lamps could traverse the treated area shining the UV lamp light onto the surface of the soil, looking for the tell-tale fluorescence of GFP. After experience is gained, personnel checking suspected areas should become adept in recognizing and identifying general kinds of buried munitions by the fluorescent pattern on the surface. Likewise, such personnel should be able to recognize and ignore the fluorescence caused by small explosive particles which are debris from an explosion, and which do not indicate buried explosives or munitions. When a positive indication of buried explosives or munitions is obtained, trained personnel can excavate on the spot, and render safe any munitions found.

Figure 3:
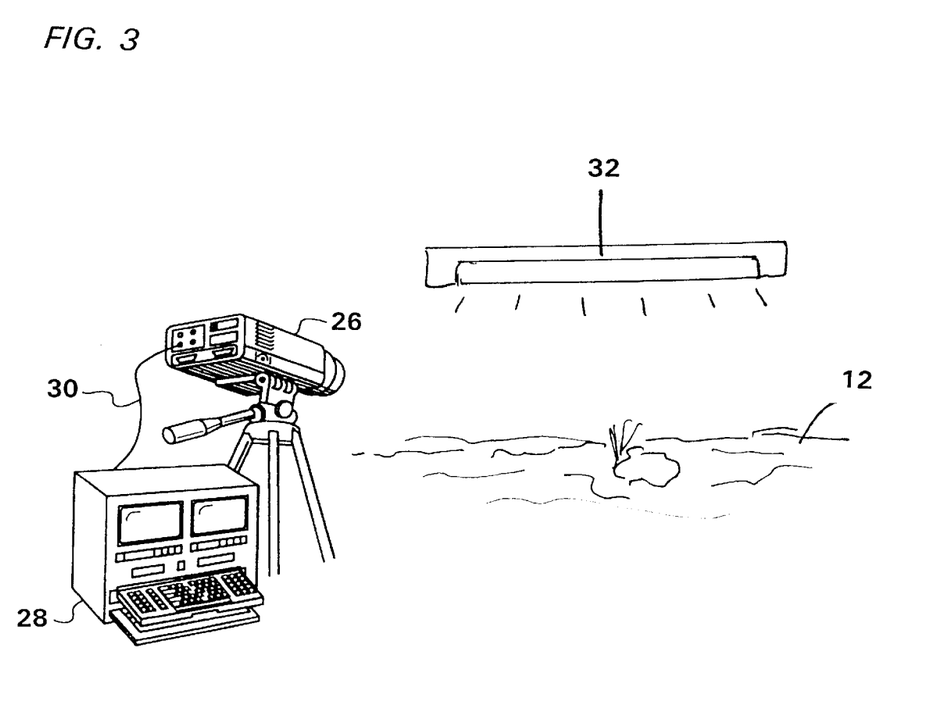
FIG. 3 is a perspective, diagrammatic view of a device for detecting the signal generated by the Biological Sensor.

Alternatively, and as shown in FIG. 3, it would be possible to construct a detector which preferably weighs between about 5 to about 10 pounds and which could be mounted on a remote or robotic vehicle for automatically detecting buried explosives or munitions. This could be accomplished using a machine vision system having a charge coupled device (CCD) camera 26 electronically linked to a computer 28, for example via a cable 30, through an analog to digital (AD) converter for digitizing, processing, and analyzing the recorded images. This system takes advantage of the fact that GFP fluorescence can be switched on and off by turning the UV light source on and off. By turning the UV light on and off during image capture, the GFP fluorescent objects will appear and disappear in sequential images, while the non-fluorescent objects illuminated by ambient light will not. Thus, by subtracting sequential images, the objects lit by ambient light will disappear, leaving only the objects illuminated by UV fluorescence. A sensitive CCD camera 26 will detect the fluorescence.

The CCD camera 26 would initially be a gated, intensified charge coupled device (CCD) area camera, coupled to a bandpass filter (not shown) for filtering the image in the GFP fluorescence emission region of the spectrum (509 nm). An area camera is initially preferred to a line scan camera, since an area camera would be better suited for early system requirements and characterization. However, a less expensive line scan camera can be substituted after characterization has been achieved, and is preferred if the detector is moving while images are captured. UV illumination could be provided by a fixture 32 containing UV fluorescent bulbs for illuminating the surface of the soil. Alternatively, it should be possible to use a UV laser as a source of UV illumination. A video recorder could also be used to capture the analog images, along with mapping data, for later analysis by the computer. If the system is in motion during image capture, sequential pairs will need to be registered with each other before they can be subtracted. The mapping data will be used to perform the registration. Following subtraction, images of the remaining GFP objects will be subjected to image analysis and pattern recognition to determine the kind of buried munition.

If desired, it is also possible to increase the concentration of explosive vapors contained in the soil (i.e., speed up their release from buried munitions or explosives) by irradiating the area suspected of containing such munitions and explosives with electromagnetic radiation. For example, a beamforming antenna could be employed to direct high-frequency to long wavelength microwave radiation, at the area suspected of containing buried munitions, such as landmines, to gently warm the area being checked and increase explosive vapor leakage from buried munitions prior to applying the bacteria. Increasing the concentration of vapor in the soil surrounding a buried munition will produce a stronger signal following the reaction with the biological sensor.

Definitions

The term "biosensor" or "biological sensor," as used herein, refers to a living cell that responds to a chemical from an explosive by producing a detectable signal. The basis for the capability of the biosensor to detect explosive chemicals is the expression of a bioreporter sequence which is operably linked to a nucleic acid sequence that is induced by a chemical from the explosive. A "chemical from the explosive," is inclusive of the explosive chemical and its degradation products.

The term "gene" refers to a DNA sequence that comprises control and coding sequences necessary for the production of a polypeptide. With reference to the bioreporter sequence, the polypeptide can be encoded by a full length coding sequence or by any portion of the coding sequence so long as, where the protein is desired to perform an activity, the desired activity is retained.

The term "bioreporter sequence" refers to the DNA coding sequence for a protein ("bioreporter protein") which functions to produce a detectable signal. As used herein, the bioreporter proteins "report" the induction of transcription of a gene of interest. In the present invention, optically detectable signals produced by reporter proteins are preferred. Suitable bioreporter proteins include but are not limited to fluorescent, bioluminescent, or chromogenic agents. A bioluminescent agent produces visible light by a biochemical process. A fluorescent agent produces a longer wavelength of light when it is excited by a shorter wavelength of light. An organism that produces the reporter protein is herein referred to a "bioreporter."

The term "gene of interest," as used herein, refers to any gene, the manipulation of which may be deemed desirable for any reason, by one of ordinary skill in the art.

The term "gene fusion" is used herein in referring to two or more genes or portions of genes that code for different polypeptide products. The technique of "gene fusion" combines the genes or gene portions in a manner that subjects them to control by the same regulatory systems.

As used herein, the term "vector" is used to refer to nucleic acid molecules that are capable of transferring DNA sequence(s) from one cell to another.

As used herein, the term "polymerase chain reaction" ("PCR") or "PCR analysis" refers to the method of K. B. Mullis disclosed in U.S. Pat. Nos. 4,683,195, 4,683,202 and 4,965,188, all of which are hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double-stranded target sequence. To effect amplification, the mixture is denatured and the primers then are annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified."

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, cloning of specific genes, searching for expressed genes, etc.

The term "recombinant DNA molecule" as used herein refers to a DNA molecule which is comprised of segments of DNA joined together by means of molecular biological techniques. A "recombinant organism" or "recombinant strain" refers to a strain of organisms comprising recombinant DNA.

As used herein, the term "cis" is used in reference to the presence of genes on the same DNA molecule. The term "cis-acting" is used in reference to the controlling effect of a regulatory gene on a gene present on the same DNA molecule. For example, promoters, which affect the synthesis of downstream mRNA are cis-acting control elements.

The term "operably linked" as used herein refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the terms "restriction endonucleases" and "restriction enzymes" refer to bacterial enzymes, each of which cut double-stranded DNA at or near a specific nucleotide sequence.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

The term "stress protein" is used with reference to a class of proteins which are expressed in response to an exposure of a cell to an adverse condition (e.g., high temperature).

After exposure, transcription of certain genes is induced and the stress proteins are expressed.

As used herein, the term "culture" is used in reference to the in vivo or in vitro growth of organisms, including, but not limited to bacteria. It is intended that the term encompass any form of microbial culture. It is intended that the term encompass the propagation of microorganisms or other living cells in media and in an environment that is conducive to their growth. Such cultures may be grown in any format, including but not limited to agar plates, broths, and semi-solid media, and may be grown in any environment suitable for the organisms cultured (i.e., aerobic, anaerobic, microaerophilic, etc.).

The Biosensor

The biosensor of the invention is a recombinant organism capable of responding to contact with a low concentration of a chemical (e.g., TNT) from an explosive. The biosensor reports on the location of the chemical by producing a detectable signal that can be measured without perturbing the position of the biosensor. A visually-detectable signal, such as bioluminescence or fluorescence, is preferred. Bioluminescence and fluorescence are rarely produced from the environmental terrain itself, so that background signal is not a significant problem.

When the biosensor contacts the chemical, certain genetic components of the biosensor respond with the initiation of transcription. Interaction of at least two categories of genetic components is contemplated in the biosensor. A first category is involved in recognition of the chemical, resulting in the induction of transcription. A second category is involved in producing a detectable signal after the chemical is recognized. The induction of transcription within the first genetic component results in transcription of the second genetic component to produce a gene product which, when expressed, provides the detectable signal. Thus, expression of the second genetic component is under the control of regulatory elements from the first genetic component.

The first genetic component may be found in a naturally occurring organism, wherein the first genetic component enables the organism to respond to the chemical, for example by using the chemical as a nutrient source. This use may be achieved, for example by induction of a catabolic gene or genes that degrade the chemical to intermediates that can easily enter the standard biochemical pathways of the cell (e.g. pyruvate, acetyl CoA, succinate). Alternatively, the organism may respond to the chemical as a toxin, e.g. by inducing a gene or genes that render the chemical less toxic. Still another alternative is that the organism may respond to the chemical by producing stress protein(s) to fortify the cell against the chemical's deleterious effects.

Prokaryotic and eukaryotic organisms that respond to the chemical are contemplated as sources of the first genetic component. Appropriate organisms may be recognized by their responses to the chemical, such as degrading or visibly altering the chemical after contact with it. As used herein, "visibly altering" means producing any change that is different from a non-responsive control. Examples include producing a color change in the chemical or solubilizing it. Even cells that are killed soon after contact with the chemical may provide an appropriate source if, for example, the chemical induces stress proteins before the cells die. In a biosensor according to the method of the invention, a response of cell death can provide a useful biosensor because a detectable signal such as a fluorescent protein, produced before death, will continue to be detectable in the intact, dead cell.

Bacteria are preferred organisms for the first genetic component of the biosensor. In comparison to higher organisms, bacteria have a small, uncomplicated genome and rapid growth and many strains are known to degrade explosive chemicals (e.g., *Phanerochaete chrysosporium Burdsall,* ATCC 20696, *Phanerochaete chrysosporium,* ATCC 24725, *Citrobacter youngae,* ATCC 51597, *Providencia rettgeri,* ATCC 51595, *Morganella morganii* subsp. *sibonii* Biogroup G, ATCC 51596, *Pseudomonas pseudoalcaligenes, P. aeruginosa, P. putida, Clostridium putrificum, C. bifermentens,* and species of Rhodococcus, Arthrobacter and Corynebacterium). The wide variety of bacteria that degrade explosives provide for a broad range of operons for use as the first genetic component.

Bacterial strains demonstrate diverse responses to explosive chemicals. For example, after exposure to TNT, transcription increases in a 16S rRNA gene (rrn) in *Bacillus subtilis.* The promoter for this gene is useful to regulate bioreporter sequences for a biosensor. Also useful in response to TNT is the salt stress gene (csb) from *Bacillus subtilis.*

Eukaryotes are also contemplated as a source for the first genetic component of the biosensor. Explosives are degraded by fungi (e.g., *Phanerochaete chrysosporium* and Mycotech White rot). Eukaryotic cell lines as well as primary (i.e. uncultured) and cultured cells that respond to the chemical are also contemplated as a source of the first genetic component.

The second genetic component comprises a bioreporter sequence from a bioreporter gene and is involved in producing a detectable signal. While all types of bioreporter genes are contemplated, those involved in production of a visually-detectable signal are preferred. For example, the bioreporter genes may encode proteins which produce fluorescent or bioluminescent reactions. A biosensor can also be constructed from bioreporter genes (e.g., lacZ gene) that encode an enzyme which catalyzes a reaction with a substrate (e.g., X-galactose) and which is detected by measuring the disappearance of chromogenic substrate or the appearance of a product.

Green Fluorescent Protein (GFP), is a preferred fluorescent protein because it displays a strong, stable fluorescence when longwave ultraviolet light illuminates it (excitation: 395 nm, emission: 509 nm). The protein is stable over a pH range of 6–12, in temperatures as high as 65° C., and after chemical treatment. (R. S. Burlage et al., (1996) Soc. Photo-Optical Instr. Engineers 2835: 42–51). The green fluorescence can be detected easily, either visually or with conventional photodetectors. GFP is a peptide that becomes cyclic through an autocatalytic reaction; the cyclic peptide is highly fluorescent and requires no other substrate. In the case of GFP, cyclization to form a chromophore generally takes several hours. The speed of formation of the GFP chromophore is dependent on growth conditions and the particular organism harboring the gene for GFP. GFP derived from the jelly fish, *Aequorea victoria,* has been cloned, sequenced and extensively characterized. (See e.g., Gene 111:229–233; M. Chalfie et al., Science 263:802–805 (1994) and Genbank Accession #M62654). (See also, U.S. Pat. No. 5,491,084 to Chalfie et al., herein incorporated in its entirety). A GFP from *Renilla reniformis* has also been characterized. (W. W. Lorenz et al. (1991) Proc. Nat'l. Acad. Sci. USA 88:4438–4442; R. M. San Pietro et al., (1993) Photochem. Photobiol. 57:63S).

Also contemplated for this invention are bioreporter sequences which encode red-shifted-GFP (RS-GFP).

RS-GFP is an altered form of the GFP which excites at a higher wavelength (excitation: 490 nm, emission: 505 nm). The RS-GFP gene is available on a plasmid, pTU58K, from ClonTech (Palo Alto, Calif.). Another mutant form of GFP displays blue fluorescence. (R. Heim, et al., (1994) Proc. Natl. Acad. Sci. USA 91:12501–12504).

Also contemplated for this invention are bioreporter genes from bioluminescent bacteria. Bioluminescent bacteria contain lux genes, which encode proteins needed to produce a bioluminescent reaction. (E. A. Meighen, (1991) Microbiol. Rev. 55:123–142; E. A. Meighen, (1994) Ann. Rev. Genet. 28:117–139). For example, Vibrio fischeri contains a lux operon which contains five genes, luxCDABE, all of which must be efficiently expressed for appropriate functioning of the bioreporter. (R. S. Burlage et al. (1994) Ann. Rev. Microbiol. 48:291–309). The lux genes are appropriate for use in an aerobic environment.

A biosensor according to the invention is produced using gene fusion techniques to join the first and second genetic components. Standard methods are used to clone DNA, join the fragments, and insert cloned DNA into the host strain. (Sambrook et al., (1989) Molecular Cloning, A Laboratory Manual). The host strain and the source for the first genetic component are usually the same, since this strain contains the regulatory elements, gene(s) and proteins which interact with the first genetic component. Alternatively, the regulatory elements can be cloned and inserted into an accessory strain (i.e., a strain different from the strain used as a source for the first genetic component) along with the fused first and second genetic components. This alternative is preferred, for example, when it would be advantageous to use an accessory strain having a desirable characteristic (e.g., cold resistance) as the host strain.

Gene fusion of the first and second genetic components is accomplished by any method which is most convenient upon consideration of the sources of genetic material available. For example, gene fusion may be accomplished by joining the first and second gene components and cloning the DNA into a plasmid vector. Alternatively, gene fusion may be accomplished by preparing a transposon containing the second gene component (the bioreporter gene), inserting the transposon into the strain containing the first genetic component, and selecting for the clones containing the appropriate fusion (i.e., clones that, when induced by the chemical, produce the identifiable signal of the reporter gene).

The biosensor of the present invention utilizes the regulatory elements of the first genetic component. These regulatory elements generally include at least the promoter region and the translational start region. The desired recombinant has the bioreporter gene(s) inserted in the correct reading frame so that a faithful copy of the bioreporter protein(s) is made after translation. As an example, the lux genes of Vibrio fischeri are joined downstream of a gene or genes from another bacterial strain, (e.g., Pseudomonas) which is regulated by an inducible promoter. Expression of the lux genes is under transcriptional control of the promoter and, when expressed, produce visible light.

Methods of cloning genes are well known in the art. (Sambrook et al., (1989) Molecular Cloning, A Laboratory Manual, 2d Edition). Briefly, the host cell genome is cut into small fragments, such as by restriction enzymes, and the fragments are individually cloned into plasmid vectors. The desired fragment contains the gene of interest, a promoter region for the initiation of transcription, and all the regulatory sites that are necessary for accurate transcription of the gene. Cloning of fragments may be performed randomly, followed by screening for a fragment that responds to the presence of a chemical from an explosive. Alternatively, a labeled probe may be used to select for fragments having a desired gene sequence, and this smaller population of candidate fragments may be cloned and screened for the desired fragment containing the gene of interest.

PCR analysis is also contemplated as a method for cloning the desired DNA fragment in those cases where sufficient DNA sequence data is known so that appropriate PCR primers can be designed. The desired DNA fragment is amplified by PCR. Cloning the DNA fragment into a plasmid vector proceeds according to conventional methods. As an example, the Bacillus subtilis rrn gene is cloned into a vector containing the gfp gene or the lux genes.

Alternatively, reverse transcriptase PCR (RT-PCR) may be used to produce amplified cDNA from RNA that is synthesized only after inducing the cell source of the first genetic component with a chemical from the explosive. This procedure requires screening and must be thoroughly checked against a control since many genes are expressed both with and without the chemical present. The PCR amplification product is cloned into a plasmid vector for the gene fusion.

As an alternative to preparing plasmids, gene fusion may be accomplished by means of a transposon containing the bioreporter sequence, to randomly mutagenize host cell DNA containing the first genetic component. The transposon may, but does not have to, additionally contain a gene which encodes a selectable marker. Examples of selectable marker genes are genes for antibiotic resistance. When the transposon contains a gene for antibiotic resistance, selection of the cells of interest is initially made by selecting for cells exhibiting the antibiotic resistance of the transposon. All successful transposed clones are then screened for the induction of the bioreporter sequence. Somewhere between about 1 in 1,000 to 1 in 10,000 clones will produce a positive response. Confirmation that the positive clone contains the genes of interest is made by cloning and sequencing the DNA and further testing for inducibility, using methods well known in the art.

When the first genetic component is from a eukaryotic cell, (e.g., yeast, fungi), the basic cloning steps are the same but modifications appropriate for eukaryotic cells are applied (e.g., eukaryotic growth media, extended time for cell growth). It is recognized that the larger and more complex genomes of eukaryotes makes screening the cells more time consuming and laborious.

It is also contemplated that the biosensor of the invention may be adapted for use in anaerobic environments. Under anaerobic conditions, the preferred host strain for the biosensor is an anaerobe (e.g., Clostridium) and the bioreporter does not require oxygen to produce a detectable signal (e.g., autocatalytic GFP or collagen).

Experimental

The following examples serve to illustrate certain preferred embodiments and aspects of the present invention and are not to be construed as limiting the scope thereof. Standard terms are employed, understandable to those skilled in the art.

In the experimental disclosure which follows, the following abbreviations apply: ATCC (American Type Culture Collection); bp (base pairs); GFP (Green Fluorescent Protein); kb (kilobases); LB (Luria-Bertani broth); $\mu$g/ml (micrograms per milliliter); mob (cis-acting mobilization sequence); nm (nanometers); PBS (phosphate buffered saline); Tc (tetracycline); Tn (transposon); tnp (transposase-encoding gene); UV (ultra violet).

EXAMPLE 1

Construction of Two Transposon Vectors Containing the Gene for GFP

Gene fusions can be accomplished by transposons that permit transcriptional (e.g., luxAB) or protein (e.g., lacZ) fusions with the gene of interest. Transposon vectors are most useful when they combine an easily assayed bioreporter gene with efficient transposition and stable integration qualities.

In order to obtain a transposon that allows random insertion of the GFP gene in bacterial genomes, two transposon vectors were constructed. Both contained the gene for GFP from the jelly fish, *Aequorea victoria*. TnGFP1 is a derivative of Tn5 that contains the promoterless GFP gene and the gene for tetracycline (Tc) resistance. (The gene for tetracycline resistance may also be represented as TetA/TetR). TnGFP2 is a similar construction derived from the mini Tn5 transposon. For this demonstration, both transposons are on narrow host range plasmids that cannot be stably maintained in hosts other than *E. coli*.

TnGFP1 (FIG. 4A and FIG. 5) was constructed from the Tn5-B21 transposon (Simon et al., 1989). Tn5-B21 was digested with the restriction enzymes BamHI and BamHI/EcoRI separately. The BamHI fragment (approximately 7 kb), containing cat, mob, gen was isolated from an agarose gel using Spin Bind DNA Extraction Units (FMC Bioproducts, Rockland, Me.). The BamHI/EcoRI fragment (approximately 5.5 kb), containing tnp and tetA/tetR, was also isolated from the gel. The gene for GFP was obtained by cutting the pGFP plasmid (Clontech, Palo Alto, Calif.) with BamHI/EcoRI, yielding a 750 bp fragment that contains the GFP gene. These three fragments were ligated together and transformed into *E.coli* NM522 (Stratagene, La Jolla, Calif.). The resulting TnGFP1 was directly electroporated into Pseudomonas strains, or transformed further into *E. coli* SM10 (Miller and Merkalanos, 1988) and subsequently introduced into Pseudomonas by conjugation.

TnGFP2 (FIG. 4B) was constructed from a Mini-Tn5 derivative (Lorenzo et al., 1990) to make a construct similar to TnGFP1. The pGFP plasmid was digested with SmaI and StuI and the resulting 750 bp fragment containing the GFP gene was ligated to NotI linker-d(pAGCGGCCGCT) SEQ ID NO:1 (New England Biolab, Beverly Mass.). Mini-Tn5 luxAB (Lorenzo et al., 1990) was digested with NotI to delete luxAB and ligated with the 750 bp NotI fragment containing the GFP gene and then transformed into *E. coli* SM10. This resulting construct, TnGFP2, was delivered into host strains by either electroporation or by conjugation and was selected on the basis of its tetracycline resistance. [FIG. 4B shows the inverted repeats (IR), the Tn5 0 end (0), and the Tn5 I end (I).]

Figure 4:
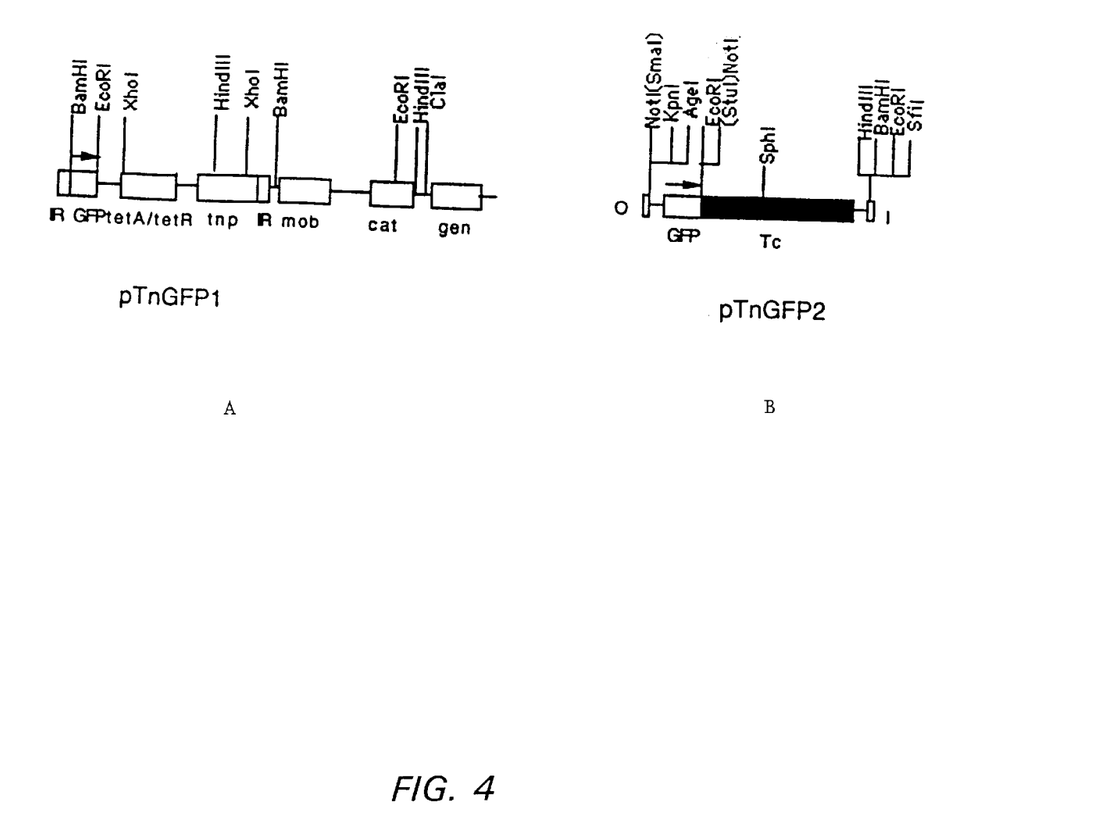
FIG. 4 is a graphic map of two transposon vectors containing a gene for GFP.
Figure 5:
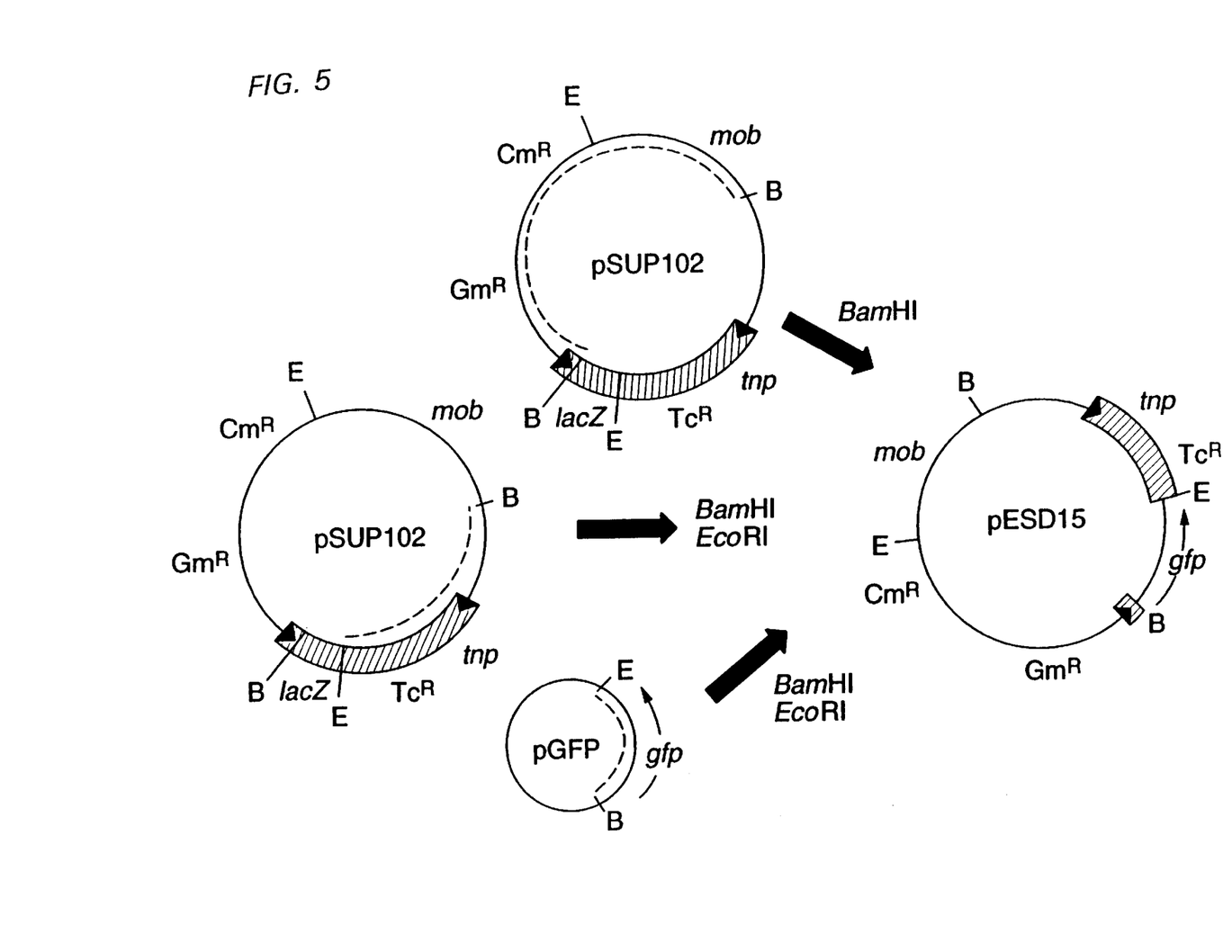
FIG. 5 is a map showing construction of the GFP transposons including the plasmid vector.

The two TnGFP transposons had the 700 bp gene cassette for GFP located at one end of the transposon, with the direction of the transcription as shown in FIG. 4. The transposon also had a tetracycline resistance gene (tetA/tetR) and a transposase (tnp). The associated plasmid had resistance genes for chloramphenicol (cat) and gentamicin (gen), and a site for mobilization of the plasmid by conjugation (mob). This plasmid can only be maintained in *E. coli* and closely related genera; in other hosts it acts as a suicide vector.

TnGFP 1 and TnGFP2 were delivered into *Pseudomonas putida* mt-2 (ATCC #33015). For electroporation, transformants were selected on LB with Tc (50 μg/ml) (Sambrook et al., 1989) using a BTX 600 (San Diego, Calif.) electroporation system. For conjugation, transformants were selected on Pseudomonas Isolation Agar (Difco, Detroit, Mich.) with Tc (100 μg/ml) for *P. putida* transformants, following a procedure described by Lorenzo et al. (1990).

For screening of transformants, colonies were illuminated with UV light. Fluorescence resulted from GFP expression as well as from the natural fluorescence of pseudomonads. To compare fluorescence, colonies were either resuspended in phosphate buffered saline (PBS) (Sambrook et al., 1989) or cultures were grown in LB broth with tetracycline for 1–2 days before diluting in PBS at an optical density (600 nm) between 0.1 and 0.3. Samples were excited at 395 nm and the emission spectrum was measured at 509 nm using a Perkin Elmer Luminescence Spectrometer LS50. Mutants were selected which demonstrated fluorescence at levels 2–5 times higher than wild type. Fluorescence was also observed using an epifluorescent microscope (Nikon Fluephot).

Transformants were obtained that expressed GFP under the control of a host promoter. The strains tested also displayed a high absorption spectrum at 509 nm when they were excited at 395 nm. Because of the high background fluorescence of the transformants, the colonies were tested individually using the luminescence spectrometer. The new transposons were successful in creating transcriptional fusion mutants showing high GFP expression in Pseudomonas. These transposons are useful, as well, in other Gram negative bacteria that can be mutagenized with Tn5.

This experiment demonstrates the successful construction of transposons carrying an easily identifiable reporter gene. These transposons are useful for gene fusion with a genetic component that is induced by a chemical from an explosive composition. To select for colonies inducible by TNT, the colonies are replicatively plated onto agar medium with or without TNT and screened for fluorescence (as described in Example 2). Colonies that fluoresce on agar containing TNT and not on agar without TNT are useful as a biosensor for detecting explosives.

EXAMPLE 2

Constructing a Recombinant Bioreporter Responsive to TNT

The salt stress gene (csb) of the bacterium *Bacillus subtilis* has been sequenced. (Akbar and Price, 1996, Gene 177:123–128 and Genbank Accession #L77099). The sequence was examined for reliable PCR primers to obtain the regulatory element of interest using a commercial search engine. The PCR primer sequence chosen for two primers is as follows:

| | |
|---|---|
| 5'-CCATCCGTCTGTCATAATGGCAG-3' | SEQ ID NO:2 |
| 5'-TGATCTGCTGAAGCGTGTCATC-3' | SEQ ID NO:3 |

The gene sequence is amplified from *Bacillus subtilis* chromosomal DNA by the method of PCR. The sequence of interest is amplified using standard PCR reagents and the primers shown above (94° C. for 1 min for dissociation; 55° C. for 1 min for reannealing; 72° C. for 2 min for extension; 30 cycles).

The amplified product is cloned into a plasmid cloning vector and sequenced to confirm the identity of the DNA of interest. The csb regulatory element is excised using restriction enzymes (EcoRI and BamHI) which recognize sites in the polylinker region of the cloning vector. The excised fragment is then cloned into a pGFP plasmid vector such that the csb promoter sequence is ligated upstream of and in-frame with the nucleotide sequence encoding the GFP. Techniques known in the art are used to transform *E. coli* DH5 with the plasmid vector, select transformants and isolate the plasmid DNA from the transformants. *Bacillus subtilis* is transformed with the plasmid DNA using an electroporation system and selection of transformants is performed.

Transformed bacteria are tested for their response (fluorescence) to TNT on agar medium. TNT is incorporated into the agar medium and the bacterial clones are spotted on the surface. (For explosive chemicals that are insoluble in aqueous base, an appropriate solvent is used to solubilize the chemical to make a concentrated stock solution and a dilute solution of the stock is applied to the agar medium). TNT (and related compounds) are tested at varying concentrations (from a maximum concentration of 100 parts per million (ppm) and decreasing by orders of magnitude) to determine the threshold concentration that induces a fluorescent signal.

After spotting on the surface, the bacterial colonies are left for 2–3 hours. Then the whole plate is illuminated with UV light to check for any fluorescent colonies. (For constructs that use a bioluminescent bioreporter sequence on the transposon, after spotting the transformed bacteria, the agar plate is kept in a black box or developer's black bag and each colony is checked using a fiber optic cable of a very sensitive photomultiplier.

One skilled in the art will recognize at once that it would be possible to construct devices to use the method of the present invention from a variety of materials and in a variety of different ways, or to modify one or more steps of the method of the present invention. While the preferred embodiments have been described in detail, and shown in the accompanying drawings, it will be evident that various further modification are possible without departing from the scope of the invention as set forth in the appended claims.

We claim:

1. A method of detecting explosives buried beneath the surface of the ground, comprising:

spraying a biological sensor comprising a recombinant bacterial organism that responds to contact with said explosives by producing a detectable signal, on the surface of the ground in an area believed to be contaminated by said buried explosives, so that the biological sensor contacts soil of said surface of said ground believed to contain the buried explosives;

allowing a sufficient time to pass to enable the biological sensor to react with explosive residue in said soil to produce a visually detectable signal; and examining said surface of the ground believed to contain said buried explosives for said visually detectable signal.

2. The method of claim 1 wherein said buried explosives comprise unexploded munitions.

3. The method of claim 1 wherein said biological sensor produces a protein which fluoresces after exposure to fluorescence excitation.

4. The method of claim 3 wherein the step of examining said surface of said ground believed to contain said buried explosives is performed by using ultraviolet light to check for fluorescence.

5. The method of claim 3 wherein said biological sensor is applied to the surface of the ground during hours of reduced sunlight between twilight and dawn.

6. The method of claim 3 wherein said protein is a fluorescent protein.

7. The method of claim 3, wherein said protein is Green Fluorescent Protein.

8. The method of claim 1 wherein said protein is a bioluminescent protein.

9. The method of claim 1 wherein said biological sensor is a genetically engineered bacterium selected from the group consisting of Pseudomonas, *Escherichia coli,* and Bacillus.

10. The method of claim 6 wherein said sufficient time is from about 2 hours to about 3 days.

11. The method of claim 1 additionally including as a preliminary step gently irradiating the area suspected of containing buried explosives with electromagnetic energy in order to increase explosive vapor concentration in the soil above and around the buried explosive, prior to applying the biological sensor to the surface.

12. The method of claim 11 wherein said electromagnetic energy varies from high-frequency to long wavelength microwave.

13. The method of claim 1 wherein said step of examining the surface of the area for a visually detectable signal is performed by using a source of ultraviolet light.

14. The method of claim 1, wherein said chemical from an explosive is selected from the group consisting of trinitrotoluene, hexahydro-1,3,5-trinitro-1,3,5-triazine and octahydro-1,3,5-trinitro-1,3,5,7-tetrazocine.

15. A method of detecting explosives buried beneath the surface of the ground, comprising the steps of:
  1) spraying a biological sensor comprising a recombinant bacterial organism that responds to contact with said explosives by producing a detectable signal on the surface of the ground in an area believed to contain said buried explosives, wherein said surface of said ground is believed to be contaminated by vapors from said explosives, under conditions such that said biological sensor contacts the soil of said surface of said ground believed to contain the buried explosives;
  2) allowing a sufficient time to pass to enable the biological sensor to react with explosive residue from said buried explosives in said soil to produce a visually detectable signal; and
  3) examining said soil of said ground surface believed to contain said buried explosives for said visually detectable signal.

16. The method of claim 15, wherein said buried explosives comprise unexploded munitions.

17. The method of claim 15 wherein said biological sensor produces a protein which fluoresces after exposure to fluorescence excitation.

18. The method of claim 17, wherein said protein is a fluorescent protein.

19. The method of claim 18, wherein said protein is a bioluminescent protein.

20. The method of claim 18, wherein the step of examining said surface of said ground believed to contain said buried explosives is performed by using ultraviolet light to observe for fluorescence.

21. The method of claim 18, wherein said biological sensor is a genetically engineered bacterium selected from the group consisting of Pseudomonas, Escherichia, and Bacillus.

22. A method of detecting explosive residue in soil comprising the steps of:
  a) providing:
    i) a biological sensor comprising a recombinant bacterial strain, and
    ii) a soil sample suspected of containing detectable levels of explosive residue; and
  b) contacting said soil sample with said biological sensor under conditions such that a detectable signal is produced in the presence of said detectable levels of explosive residue.

23. The method of claim 22, further comprising the step of detecting said detectable signal.

24. The method of claim 22, wherein said explosive residue comprises unexploded munitions.

25. The method of claim 22, wherein said explosive residue is selected from the group of explosives consisting of trinitrotoluene, hexahydro-1,3,5-trinitro-1,3,5-triazine, and octahydro-1,3,5-trinitro-1,3,5,7-tetrazocine.

26. The method of claim 22, wherein said biological sensor produces a protein which fluoresces after exposure to fluorescence excitation.

27. The method of claim 22, wherein said protein is a fluorescent protein.

28. The method of claim 22, wherein said protein is a bioluminescent protein.

29. A method of detecting explosive residue in soil comprising the steps of:
  a) providing:
    i) a biological sensor comprising a recombinant bacterial strain, wherein said recombinant bacterial strain is selected from the group consisting of recombinant Pseudomonas, Escherichia and Bacillus, and
    ii) a soil sample suspected of containing detectable levels of explosive residue; and
  b) contacting said soil sample with said biological sensor under conditions such that a detectable signal is produced in the presence of said detectable levels of explosive residue.

30. A biological sensor for detecting explosives comprising a recombinant bacterial strain that responds to contacting a chemical from an explosive by producing a detectable signal, wherein said recombinant bacterial strain is selected from the group consisting of recombinant Bacillus, Pseudomonas, and *Escherichia coli.*

31. The sensor of claim 30 wherein a bacterial cell of the recombinant bacterial strain comprises a regulatory element from a gene that is inducible by the chemical, the regulatory element being operably linked to a bioreporter sequence encoding a protein that functions to produce the detectable signal.

32. The sensor of claim 31, wherein said protein produces a fluorescent signal.

33. The sensor of claim 31 wherein said protein produces a bioluminescent signal.

34. The biological sensor of claim 31, wherein said protein is Green Fluorescent Protein.

35. A biological sensor for detecting explosives comprising a recombinant bacterial strain that responds to contacting a chemical from an explosive by producing a detectable signal, wherein said recombinant bacterial strain is selected from the group consisting of recombinant Bacillus, Pseudomonas, and *Escherichia coli,* and wherein said chemical from said explosive is selected from the group consisting of trinitrotoluene, hexahydro-1,3,5-trinitro-1,3,5-triazine and octahydro-1,3,5-trinitro-1,3,5,7-tetrazocine.

36. The sensor of claim 35, wherein a bacterial cell of said recombinant bacterial strain comprises a regulatory element from a gene that is inducible by the chemical, said regulatory element being operably linked to a bioreporter sequence encoding a protein that functions to produce the detectable signal.

37. The sensor of claim 36, wherein said protein produces a fluorescent signal.

38. The sensor of claim 36, wherein said protein produces a bioluminescent signal.

39. The sensor of claim 36, wherein said protein is Green Fluorescent Protein.

* * * * *